United States Patent [19]

Orrico

[11] Patent Number: 5,775,910
[45] Date of Patent: Jul. 7, 1998

[54] DENTAL POST

[76] Inventor: Anthony J. Orrico, 112 Quayside Dr., Jupiter, Fla. 33477

[21] Appl. No.: 869,180

[22] Filed: Jun. 4, 1997

[51] Int. Cl.$^6$ .................................................. A61C 5/08
[52] U.S. Cl. ................................................... 433/221
[58] Field of Search ................................... 433/220, 221

[56] References Cited

U.S. PATENT DOCUMENTS

| Re. 31,948 | 7/1985 | Deutsch et al. | 433/221 |
|---|---|---|---|
| 1,397,067 | 11/1921 | Williams | 433/221 |
| 1,479,508 | 1/1924 | Maeulen et al. | 433/221 |
| 2,705,837 | 4/1955 | Gerlach | 433/221 |
| 4,103,422 | 8/1978 | Weiss et al. | 433/215 |
| 4,479,783 | 10/1984 | Weissman | 433/221 |
| 4,480,997 | 11/1984 | Deutsch et al. | 433/221 |
| 4,490,116 | 12/1984 | Deutsch et al. | 433/215 |
| 4,600,391 | 7/1986 | Jacob | 433/220 |
| 4,708,655 | 11/1987 | Weissman | 433/225 |
| 4,744,756 | 5/1988 | Ross | 433/173 |
| 4,752,225 | 6/1988 | Bori | 433/221 |
| 4,759,714 | 7/1988 | Szegvary | 433/221 |
| 4,826,434 | 5/1989 | Krueger | 433/174 |
| 4,832,602 | 5/1989 | Kurze et al. | 433/220 |
| 4,846,685 | 7/1989 | Martin | 433/221 |
| 4,871,313 | 10/1989 | Maillefer | 433/225 |
| 5,066,230 | 11/1991 | Weissman | 433/165 |
| 5,073,112 | 12/1991 | Weil | 433/221 |
| 5,145,373 | 9/1992 | Roane | 433/221 |
| 5,161,973 | 11/1992 | Johnson | 433/221 |
| 5,236,361 | 8/1993 | Mays | 433/221 |
| 5,263,996 | 11/1993 | Filhol | 433/221 |
| 5,316,478 | 5/1994 | Chalifoux | 433/221 |
| 5,326,263 | 7/1994 | Weissman | 433/224 |
| 5,453,010 | 9/1995 | Klein | 433/221 |

FOREIGN PATENT DOCUMENTS

| 305934 | 10/1987 | European Pat. Off. | 433/225 |
|---|---|---|---|
| 562605 | 3/1974 | Sweden | 433/220 |
| 662939 | 7/1985 | Sweden | 433/225 |

OTHER PUBLICATIONS

APM–Sterngold Information Sheet (Unknown Publication date) IntegraPost advertisement (Sep. 1996).

*Primary Examiner*—John J. Wilson
*Attorney, Agent, or Firm*—George Pappas

[57] ABSTRACT

An improved dental post having a radicular portion which is inserted and cemented into a root canal area of a tooth and also having a coronal portion which is used for attachment of a core to retain an artificial crown. The radicular portion includes a cervical flare shaped section, a central parallel circular shaped section and an apical tapered section. The cervical flare shaped section is adjacent the coronal portion. The radicular portion is provided with circumferentially extending grooves which communicate with longitudinally extending venting flutes. The venting flutes extend from the apical tapered section to the coronal portion. The coronal portion includes three cross shaped sections, each of which includes four protrusions extending from a central hub and forming valleys therebetween. The cross shaped section protrusions and valleys are longitudinally spaced apart and are radially aligned with one another. The radicular portion is sandblasted to facilitate using current resin-bonded cement techniques which specify a sandblasted surface for bonding.

20 Claims, 2 Drawing Sheets

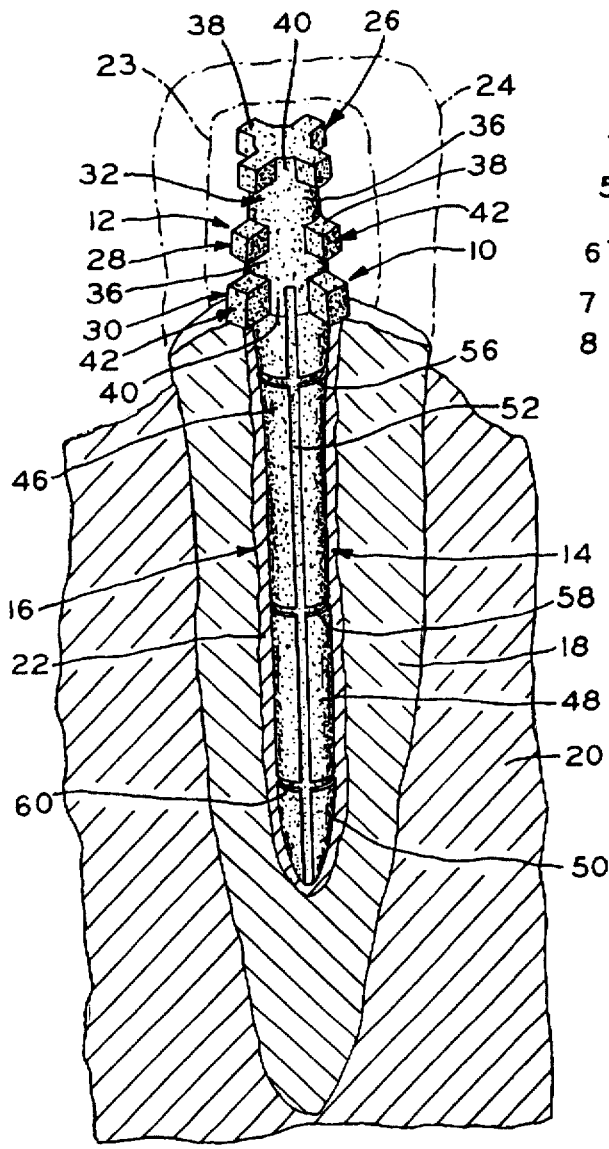
FIG_1
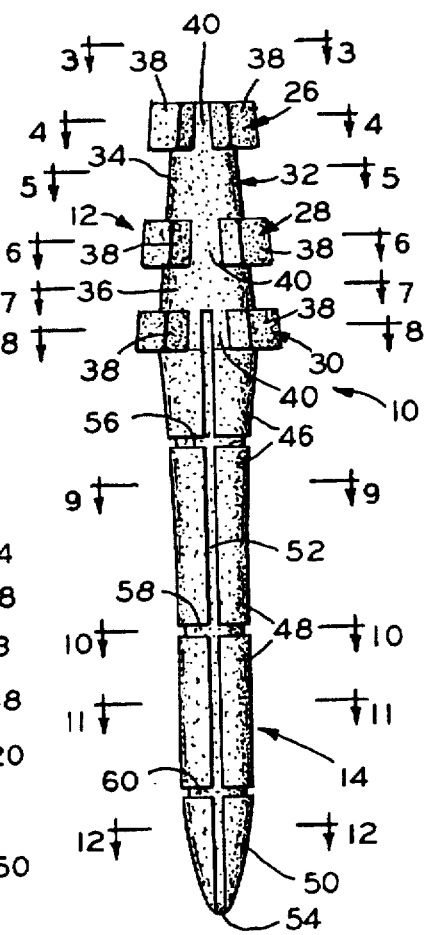
FIG_2
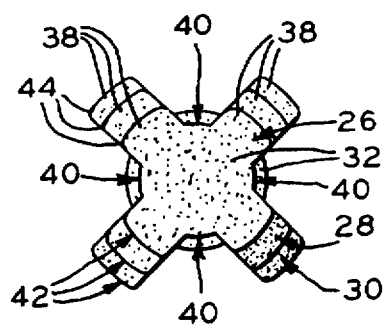
FIG_3

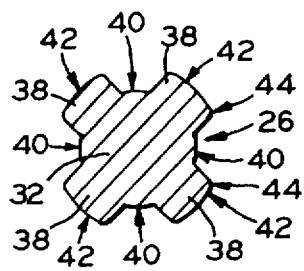 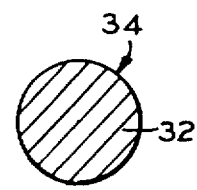 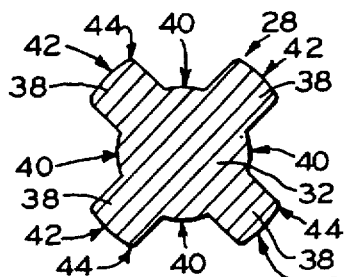
FIG_4   FIG_5   FIG_6
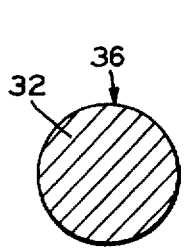 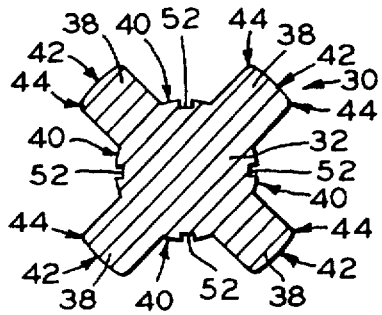 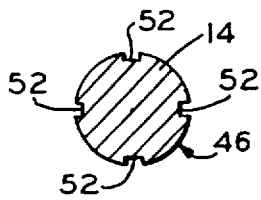
FIG_7   FIG_8   FIG_9
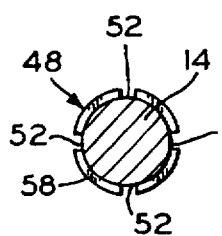 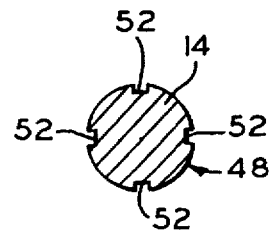 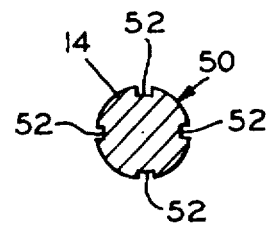
FIG_10   FIG_11   FIG_12
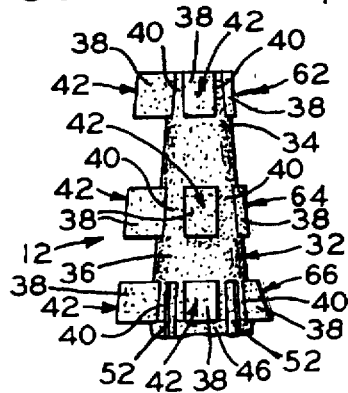
FIG_13

5,775,910

1

DENTAL POST

TECHNICAL FIELD

The device of the present invention generally relates to dental posts of the type having a radicular portion that is inserted and cemented into a root canal area of a tooth and having a coronal portion for attachment of an artificial crown thereto. More particularly, the present invention relates to a dental post having an improved overall shape for use and cementing into a root canal area of a tooth and for more effectively relieving hydraulic pressure during cementing of the dental post in the root canal area of a tooth and which has a sandblasted surface to take advantage of bonding techniques.

BACKGROUND OF THE INVENTION

Dental posts, also sometimes referred to as endodontic posts and root canal anchors, are commonly used for replacing a broken, chipped or otherwise damaged tooth with an artificial crown. In a known and customary manner, the damaged tooth coronal portion is typically removed and a root canal is performed on the root thereof. The dental post is inserted into the root canal whereat it is secured by frictional engagement means and/or cementing. Thereafter, an artificial tooth or crown of a desired shape and color is attached typically by cementing to a core retained by the coronal portion of the dental post.

Although many different types and shapes of dental posts have been made and used, a need exists for a dental post having characteristics that overall allows the dental post to be used for replacing various different teeth, is easily usable by the dentists within a more easily formed common root canal shape, readily relieves hydraulic pressure during the cementing process for more easily and better properly locating and cementing the dental post, provides a surface area in the radicular portion that allows secure attachment within the tooth root canal area, and also provides a coronal portion that readily and easily allows accurate and secure attachment of the artificial tooth thereto.

SUMMARY OF THE INVENTION

It is the principal object of the present invention to achieve the above-discussed objects and to overcome the discussed disadvantages associated with prior dental posts.

The present invention achieves the above-mentioned objects and overcomes disadvantages associated with prior dental posts by providing an improved dental post having a radicular portion for insertion and cementing into a root canal area of a tooth and having a coronal portion for attachment of an artificial tooth thereto. The radicular portion includes a cervical flare shaped section, a central parallel circular shaped section and an apical tapered section. Four longitudinal venting flutes are provided on the radicular portion and extend longitudinally over the apical tapered section, the central parallel circular shaped section and the cervical flare shaped section. The longitudinal venting flutes further extend up and into the coronal portion. Further yet, each of the longitudinal venting flutes are located radially around the radicular portion about 90° degrees from one another and each extends up into the coronal portion.

Three circumferentially extending grooves are provided on the radicular portion and each communicates with each of the longitudinal venting flutes. One of these circumferentially extending grooves is located around the cervical flare shaped section. A second circumferentially extending groove is located around the central parallel circular shaped section. The third circumferentially extending groove is located between the central parallel circular shaped section and the apical tapered section. The venting flutes which extend to the tip or end of the apical tapered section along with the circumferentially extending grooves act to both relieve hydraulic pressure between the radicular portion and the root canal area during the cementing process and, further, to provide better grip and to better secure the dental post within the root canal along with the cement or other adhesive or bonding material. To further aid in securement of the radicular portion within the root canal area of the tooth, the radicular portion surface may be sandblasted and thereby provided with a slightly rougher dimpled surface finish whereby the cement and/or other adhesive materials may better grip and bond.

The coronal portion of the dental post is located adjacent the cervical flare shaped section and is provided with preferably three cross shaped sections each of which have four protrusions extending from a central hub. Valleys are formed between each of the protrusions of each of the cross shaped sections. The three cross shaped sections are longitudinally spaced apart from one another and define neck areas located therebetween on the central hub. The protrusions and valleys of each of the three cross shaped sections are longitudinally aligned with one another. Preferably, the neck areas between the cross shaped sections are frusto-conical shaped. One of the neck areas is preferably longitudinally longer than the other. The protrusions of each of the cross shaped sections preferably include a radial peripheral portion each of which are shaped with an outer surface for collectively forming a frusto-conical shaped coronal portion. In one embodiment, one protrusion of each of the cross shaped sections which are longitudinally aligned with one another are collectively shaped so as to form a lingual concavity as viewed from the side. Similar to the radicular portion, the coronal portion may also be sandblasted for providing a slightly dimpled surface for better bonding and adhering.

The longitudinal venting flutes extend into the coronal portion through the valleys formed by the protrusions of the cross shaped section located adjacent the cervical flare sections. Accordingly, hydraulic pressure is readily and easily relieved during the cementing process by allowing excess cement to flow through the valleys of the lowermost cross shaped section adjacent the cervical flare section.

In one form thereof, the present invention is directed to an improved dental post of a type having a radicular portion for insertion and cementing into a root canal area of a tooth and having a coronal portion for attachment of an artificial tooth thereto. The dental post improvement includes the radicular portion having a cervical flare shaped section, a central parallel circular section, and an apical tapered section. The dental post coronal portion is located adjacent the cervical flare shaped section and has a plurality of cross shaped sections. Each of the cross shaped sections have four protrusions extending from a central hub and the four protrusions form valleys therebetween. A longitudinal venting flute extends over the apical tapered section, the central parallel circular shaped section and the cervical flare shaped section and through a valley between the protrusions. During cementing of the dental post in a root canal area of the tooth, hydraulic pressure between the radicular portion and the root canal area is relieved.

BRIEF DESCRIPTION OF THE DRAWINGS

The above-mentioned and other features and objects of this invention and the manner of obtaining them will become

3 more apparent and the invention itself will be better understood by reference to the following description of embodiments of the invention taken in conjunction with the accompanying drawings wherein:

FIG. 1 is a perspective view of a dental post constructed in accordance with the principles of the present invention and shown inserted and set within a root canal area of a tooth;

FIG. 2 is a side elevated view of the dental post shown in FIG. 1;

FIG. 3 is a top plan view of the dental post shown in FIG. 1;

FIG. 4 is an enlarged cross section view taken along line 4—4 in FIG. 2;

FIG. 5 is an enlarged cross section view taken along line 5—5 in FIG. 2;

FIG. 6 is an enlarged cross section view taken along line 6—6 in FIG. 2;

FIG. 7 is an enlarged cross section view taken along line 7—7 in FIG. 2;

FIG. 8 is an enlarged cross section view taken along line 8—8 in FIG. 2;

FIG. 9 is an enlarged cross section view taken along line 9—9 in FIG. 2;

FIG. 10 is an enlarged cross section view taken along line 10—10 in FIG. 2;

FIG. 11 is an enlarged cross section view taken along line 11—11 in FIG. 2;

FIG. 12 is an enlarged cross section view taken along line 12—12 in FIG. 2; and, FIG. 13 is a partial side elevation of a dental post constructed in accordance with the principles of the present invention and wherein the coronal portion is shaped having a lingual concavity.

Corresponding reference characters indicate corresponding parts throughout the several views of the drawings.

The exemplifications set out herein illustrate preferred embodiments of the invention in one form thereof and such exemplifications are not to be construed as limiting the scope of the disclosure of the scope of the invention in any manner.

DETAILED DESCRIPTION OF SPECIFIC EMBODIMENTS

Referring initially to FIGS. 1-3, a dental post constructed in accordance with the principles of the present invention, is shown and designated by numeral 10. Dental post 10 includes an upper coronal portion 12 and a lower radicular portion 14. As seen in FIG. 1, dental post 10 is designed for and is used by inserting the radicular portion 14 thereof into a root canal area 16 of a tooth 18 which is located in gums 20. The radicular portion 14 of dental post 10 is secured within the root canal area 16 with a cement or bonding agent 22. More specifically, in a known and customary manner, after the root canal area 16 has been formed within the tooth 18, a cement 22 is injected therein and the dental post is inserted within the root canal area for securement therein. Thereafter, a core 23 shown with a dashed line is formed and secured over the coronal portion 12 in a known and customary manner and an artificial tooth or crown 24, also shown with a dashed line, is secured thereover and over the tooth 18 and the coronal portion 12 of dental post 10.

The coronal portion of dental post 10, in general, is made up of three cross shaped sections 26, 28 and 30 each of which are made up of four protrusions extending radially outwardly from a central hub 32. Sections, 26, 28 and 30 are spaced longitudinally apart from one another a distance defined by the neck areas 34 and 36 formed by central hub 32. As best seen in FIG. 2, neck areas 34 and 36, along with the central hub 32, are generally frusto-conically shaped. The longitudinal length of neck areas 34 and 36 can be equal in distance or, in the alternative as shown, neck area 34 can be longitudinally longer than neck area 36.

Each of the cross shaped sections 26, 28 and 30 are made up of four protrusions 38 which, as mentioned above, extend radially outwardly from the central hub 32. The protrusions 38 of each cross shaped section as viewed from the top, form a cross and define valleys 40 therebetween on the central hub 32. As best seen in FIGS. 1-3 the protrusions 38 and valleys 40 of each of the cross shaped sections 26, 28 and 30 are radially aligned with one another.

The protrusions 38 of each of the cross shaped sections 26, 28 and 30, further include a radial peripheral portion or surface 42 which, as viewed in side elevation, collectively form a frusto-conical outer shape generally following the frusto-conical shaped of the central hub 32. All of the corners 44 of each of the protrusions 38 are also rounded as best seen in FIGS. 3, 4, 6 and 8.

The radicular portion 14 of the dental post 10 is generally elongate as shown and includes a cervical flare or frusto-conical section 46, a central parallel circular shaped section 48 and an apical tapered section 50. The cervical flare shaped section 46 is adjacent and directly below the coronal portion 12; the central parallel circular shaped section 48 is located between the apical tapered section 50 and the cervical flare shaped section 46; and, the apical tapered section 50 is located on the distal end of the radicular portion 14 and forms the tip of the dental post 10. The change in shapes from the cervical flare shaped section 46 to the central parallel circular shaped section 48 and to the apical tapered section 50 can be gradual as depicted in FIG. 2 or can be more abrupt as shown in FIG. 1.

The radicular portion 14 further includes four longitudinally extending venting flutes which extend from the tip 54 of the radicular portion 14 over the apical tapered section 50, the central parallel circular shaped section 48 and the cervical flare shaped section 46, and finally, up and through each of the valleys 40 of the lowermost cross shaped section 30 which is located adjacent the cervical flare shaped section 46. As best seen in FIGS. 8–12, the longitudinally extending venting flutes 52 are located radially around the radicular portion 14 about 90° degrees from one another.

The radicular portion 14 further includes three circumferentially extending grooves 56, 58 and 60 each of which extends around the radicular portion 14 and communicates with each of the longitudinally extending venting flutes 52. Circumferentially extending groove 56 extends around the cervical flare shaped section 46; circumferentially extending groove 58 extends around the central parallel circular shaped section 48; and, circumferentially extending groove 60 is located between the central parallel circular shaped section 48 and the apical tapered section 50.

As should now be appreciated, during the cementing process the circumferentially extending grooves 56, 58 and 60 along with the longitudinally extending venting flutes 52 act to relieve hydraulic pressure between the radicular portion 14 and the root canal area 16 by readily allowing access cement to flow up through the longitudinally extending venting flutes 52 and through the valleys 40 of the cross shaped section 30. Additionally, the circumferentially extending grooves 56, 58 and 60 and the longitudinally extending venting flutes 52 aid in the securement and bonding of the dental post 10 with the cement 22. So as to further aid the bonding with cement 22, the radicular portion 14 can be sandblasted as shown in FIGS. 1 and 2 for providing a textured or dimpled surface finish throughout. In the same manner, for aiding in the bonding and securement of the artificial tooth or crown 24, the coronal portion 12 can be sandblasted as shown for providing an overall surface finish which is textured and/or dimpled.

In the embodiment shown in FIG. 13, the coronal portion 12 of the dental post 10 is shaped having lingual or tongue aspect. In this embodiment, the cross shaped sections 26, 28 and 30 are constructed similar to the embodiment of FIGS. 1-12, except that one set of longitudinally aligned protrusions 38 are shaped to collectively form a lingual concavity as viewed from the side and as shown in FIG. 13. More specifically, one of the aligned protrusions of cross shaped section 26 is provided with a first lingual concavity shaped 62; one of the protrusions of the cross shaped section 28 is provided with a second lingual concavity shaped section 64; and, one of the aligned protrusions of the cross shaped section 30 is provided with a third lingual concavity shaped section 66. Together, the lingual concavity shaped sections 62, 64 and 66 form the overall lingual concavity shape as shown in FIG. 13.

Preferably, the dental post is made of materials such as titanium alloy, stainless steel or carbon fiber. Further, dental post 10 is preferably manufactured in different sizes such as small, medium and large. The small size dental post 10 would preferably have an overall length of 11.5 millimeters including a radicular portion of 8 millimeters and a coronal portion of 3.5 millimeters. The medium size dental post 10 would preferably have an overall size of 13 millimeters and would include a radicular portion which is 9 millimeters in length and a coronal portion which is 4 millimeters in length. The large sized dental post 10 would preferably be 16 millimeters in overall length and would include a radicular portion of 11 millimeters in length and a coronal portion of 5 millimeters in length.

While the invention has been described as having specific embodiments, it will be understood that it is capable of further modifications. This application is, therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. An improved dental post of the type having a radicular portion for insertion and cementing into a root canal area of a tooth and a coronal portion for attachment of an artificial tooth thereto, wherein the improvement comprises:

said radicular portion having a cervical flare shaped section, a central parallel circular shaped section and an apical tapered section;

said coronal portion being adjacent said cervical flare shaped section and having a plurality cross shaped sections, said cross shaped sections each having four protrusions extending from a central hub and said four protrusions forming valleys therebetween; and, a longitudinal venting flute extending over said apical tapered section, said central parallel circular shaped section and said cervical flare shaped section and through a valley between said protrusions, whereby during cementing of the dental post in a root canal area of a tooth hydraulic pressure between said radicular portion and said root canal area is relieved.

2. The improved dental post of claim 1 wherein four longitudinal venting flutes are provided, each longitudinal flute located radially around said apical tapered section, said central parallel circular shaped section and said cervical flare shaped section about 90° degrees from one another and, further, wherein each of said longitudinal venting flutes extend through a valley between said protrusions.

3. The improved dental post of claim 2 further comprising a circumferentially extending groove around said radicular portion and communicating with each of said longitudinal venting flutes.

4. The improved dental post of claim 3 wherein three circumferentially extending grooves are provided around said radicular portion and communicating with each of said longitudinal venting flutes, one of said circumferentially extending grooves located around said cervical flare shaped section, one of said circumferentially extending grooves located around said central parallel circular shaped section and one of said circumferentially extending grooves located between said central parallel circular shaped section and said apical tapered section.

5. The improved dental post of claim 4 wherein said radicular portion includes a sandblasted surface area.

6. The improved dental post of claim 4 wherein said coronal portion includes three cross shaped sections, each of said cross shaped sections having four protrusions extending from a central hub and forming valleys therebetween.

7. The improved dental post of claim 6 wherein said three cross shaped sections protrusions and valleys are longitudinally spaced apart and are aligned with one another and said central hub forms neck areas between said three cross shaped sections.

8. The improved dental post of claim 7 wherein said neck areas of said central hub are frusto-conical shaped.

9. The improved dental post of claim 8 wherein said protrusions each include a radial peripheral portion, said protrusion radial peripheral portions shaped for collectively forming a frusto-conical shaped coronal portion.

10. The improved dental post of claim 7 wherein said one central hub neck area is longitudinally longer than the other.

11. The improved dental post of claim 7 wherein three longitudinally aligned cross shaped section protrusions include radial peripheral portions which are shaped for collectively forming a lingual concavity.

12. The improved dental post of claim 2 wherein said coronal portion includes three cross shaped sections, each of said cross shaped sections having four protrusions extending from a central hub and forming valleys therebetween.

13. The improved dental post of claim 1 further comprising a circumferentially extending groove around said radicular portion and communicating with said longitudinal venting flute.

14. The improved dental post of claim 13 further comprising three circumferentially extending grooves around said radicular portion and communicating with said longitudinal venting flute, one of said circumferentially extending grooves located around said central flare shaped section, one of said circumferentially extending grooves located around said central parallel circular shaped section and one of said circumferentially extending grooves located between said central parallel circular shaped section and said apical tapered section.

15. The improved dental post of claim 1 wherein said radicular portion includes a sandblasted surface.

16. The improved dental post of claim 1 wherein said coronal portion includes three cross shaped sections, each of said cross shaped sections having four protrusions extending from a central hub and forming valleys therebetween.

17. The improved dental post of claim 16 wherein said three cross shaped sections protrusions and valleys are longitudinally spaced apart and are aligned with one another and said central hub forms neck areas between said three cross shaped sections.

18. The improved dental post of claim 17 wherein three longitudinally aligned cross shaped section protrusions include radial peripheral portions which are shaped for collectively forming a lingual concavity.

19. The improved dental post of claim 18 wherein said protrusions each include a radial peripheral portion, said protrusion radial peripheral portions shaped for collectively forming a frusto-conical shaped coronal portion.

20. The improved dental post of claim 17 wherein said neck areas of said central hub are frusto-conical shaped.

* * * * *